United States Patent
Tateda

(10) Patent No.: US 9,762,981 B2
(45) Date of Patent: Sep. 12, 2017

(54) COMMUNICATION SYSTEM AND RECEIVING DEVICE

(71) Applicant: KONICA MINOLTA, INC., Chiyoda-ku, Tokyo (JP)

(72) Inventor: Norihiro Tateda, Tama (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/314,525

(22) PCT Filed: Jun. 4, 2015

(86) PCT No.: PCT/JP2015/066130
§ 371 (c)(1),
(2) Date: Nov. 29, 2016

(87) PCT Pub. No.: WO2015/194381
PCT Pub. Date: Dec. 23, 2015

(65) Prior Publication Data
US 2017/0201811 A1  Jul. 13, 2017

(30) Foreign Application Priority Data
Jun. 18, 2014 (JP) ................. 2014-125110

(51) Int. Cl.
*H04Q 9/02* (2006.01)
*A61B 5/00* (2006.01)
(Continued)

(52) U.S. Cl.
CPC ............. *H04Q 9/02* (2013.01); *A61B 5/0015* (2013.01); *A61B 5/02055* (2013.01);
(Continued)

(58) Field of Classification Search
CPC ............. G06K 7/0008; G06K 7/10019; G06K 7/10356; G06K 7/10029; G06K 7/10039;
(Continued)

(56) References Cited

U.S. PATENT DOCUMENTS 7,338,445 B2 *  3/2008  Feliss .................... A61B 5/1112
                                                    128/903
9,384,494 B2 *  7/2016  Gomi ................. G06Q 30/0201
(Continued)

FOREIGN PATENT DOCUMENTS

JP     10099285 A    4/1998
JP     2005110816 A  4/2005
(Continued)

OTHER PUBLICATIONS

International Search Report (ISR) and Written Opinion dated Aug. 11, 2015 issued in International Application No. PCT/JP2015/066130.

(Continued)

*Primary Examiner* — Mark Blouin
(74) *Attorney, Agent, or Firm* — Holtz, Holtz & Volek PC

(57) ABSTRACT

A communication system and a receiving device ensure reducing a risk of performing pairing processing on an incorrect pair caused by presence of a large count of communication candidates, wherein the communication system includes an extractor to extract the communication candidates among a plurality of biological information measuring devices by the receiving device. The extractor compares radio field intensities of a plurality of pairing signals. A first threshold value specifies a lower limit of the radio field intensity at which a transmission of biological information is effectively achieved. The extractor extracts the at least one biological information measuring device transmitting the pairing signal at the radio field intensity exceeding a second threshold value as the communication candidate for
(Continued)

this receiving device. According to an input operation by an operator, a selector selects the one biological information measuring device as a communication target among the communication candidates extracted by the extractor.

20 Claims, 5 Drawing Sheets

(51) Int. Cl.
    *A61B 5/1455*     (2006.01)
    *A61B 5/0205*     (2006.01)
    *G06F 19/00*     (2011.01)
    *H04L 29/08*     (2006.01)

(52) U.S. Cl.
    CPC ........ *A61B 5/14551* (2013.01); *A61B 5/6826* (2013.01); *A61B 5/742* (2013.01); *G06F 19/3406* (2013.01); *H04L 67/12* (2013.01); *H04Q 2209/40* (2013.01); *H04Q 2209/84* (2013.01)

(58) Field of Classification Search
    CPC ........... G06K 19/0723; G06K 7/10009; G06K 7/10128; G06K 7/10069
    USPC ........................................................ 340/10.2
    See application file for complete search history.

(56) References Cited

U.S. PATENT DOCUMENTS

| | | | |
|---|---|---|---|
| 2012/0108917 A1 | 5/2012 | Libbus et al. | |
| 2013/0321864 A1 | 12/2013 | Jintsugawa et al. | |
| 2015/0015417 A1 | 1/2015 | Libbus et al. | |
| 2016/0039424 A1* | 2/2016 | Hong .................... | B60W 40/08 701/2 |
| 2016/0109861 A1* | 4/2016 | Kim ....................... | G04G 21/08 368/69 |
| 2017/0100636 A1* | 4/2017 | Umetsu .............. | A63B 24/0075 |

FOREIGN PATENT DOCUMENTS

| | | |
|---|---|---|
| JP | 2007060256 A | 3/2007 |
| JP | 2012511965 A | 5/2012 |
| JP | 2013247606 A | 12/2013 |

OTHER PUBLICATIONS

English tranlsation of the Written Opinion of the International Searching Authority dated Aug. 11, 2015 issued in counterpart International Application No. PCT/JP2015/066130.

* cited by examiner

COMMUNICATION SYSTEM AND RECEIVING DEVICE

TECHNICAL FIELD

The present invention relates to a communication system that includes a biological information measuring device as a transmitting device and a receiving device.

BACKGROUND ART

As a biological information measuring device mounted to a living body to measure information on this living body, there has been known a pulse oximeter, an electrocardiographic monitor, a blood pressure monitor, and the like. For example, a pulse oximeter described in Patent Literature 1 irradiates a living body part with light at a measured portion mounted to the living body part of an examinee. Based on an amount of light transmitting the living body part or reflected by the living body part, oxygen saturation (SpO2) in blood is derived.

Additionally, there has been known a receiving device (for example, a monitor) that receives a biological information signal acquired by these biological information measuring devices and performs predetermined data processing.

CITATION LIST

Patent Literature

Patent Literature 1: JP 2005-110816 A

SUMMARY OF INVENTION

Technical Problem

Wired connection between the biological information measuring devices and the receiving devices possibly limits operations of the living bodies to which the biological information measuring devices are mounted. In view of this, there may be a case where the biological information measuring devices and the receiving devices are separately disposed, and the biological information measuring devices communicate with the receiving devices through wireless communications. In this case, prior to transmission of the biological information signals from the biological information measuring devices to the receiving devices, pairing processing is performed between both. For example, there has been known the following pairing processing method. An operator operates the receiving device to select one biological information measuring device as a communication target among a plurality of communication candidates (the plurality of biological information measuring devices) displayed on a display of the receiving device.

However, at a field where the biological information measuring devices and the receiving devices are used (for example, a hospital), a large number of the biological information measuring devices are generally disposed in a comparatively close range (for example, in the identical facility). Accordingly, caused by the presence of a large number of communication candidates, a risk that the operator incorrectly selects the communication target has been generated.

The present invention has been made to solve the above-described problem, and an object of the present invention is to provide a communication system and a receiving device that can reduce a risk of performing the pairing processing on an incorrect pair caused by the presence of a large number of communication candidates.

Solution to Problem

To solve the above problem, according to a first aspect of the present invention, there is provided a communication system including: a biological information measuring device configured to transmit a pairing signal and a biological information signal by wireless communications, the pairing signal including pairing information to establish the wireless communications, the biological information signal including biological information acquired through measurement; and a receiving device configured to receive the pairing signal transmitted from the biological information measuring device, the receiving device being configured to establish the wireless communications with the biological information measuring device to receive the biological information signal transmitted from the biological information measuring device, wherein the receiving device includes: a detector configured to detect a radio field intensity of the received pairing signal; an extractor configured to compare a second threshold value with the radio field intensities of the plurality of pairing signals when the plurality of pairing signals are detected by the detector, the second threshold value being larger than a first threshold value, the first threshold value specifying a lower limit of the radio field intensity at which the transmission of the biological information is effectively achieved, the extractor being configured to extract the at least one biological information measuring device transmitting the pairing signal at the radio field intensity exceeding the second threshold value as a communication candidate for the receiving device; a selector configured to select the biological information measuring device as a communication target among the at least one extracted biological information measuring device; and a communication unit configured to receive the biological information signal transmitted from the biological information measuring device by the wireless communications.

According to a second aspect of the present invention, in the communication system according to the first aspect of the present invention, the receiving device is configured to enter a routine to establish the wireless communications triggered by the reception of the pairing signal transmitted from the biological information measuring device by the receiving device.

According to a third aspect of the present invention, in the communication system according to the first or the second aspect of the present invention, the selector is configured to select the biological information measuring device that transmits the pairing signal at a largest radio field intensity among the two or more biological information measuring devices when the extractor extracts the two or more biological information measuring devices as the communication candidates.

According to a fourth aspect of the present invention, in the communication system according to the first or the second aspect of the present invention, the receiving device further includes a display and an operating unit, and when the extractor extracts the two or more biological information measuring devices as the communication candidates, the selector is configured to cause the display to display two or more identification indices corresponding to the respective two or more biological information measuring devices extracted as the communication candidates, the selector being configured to select the biological information measuring device based on an input operation from the operating unit by an operator.

According to a fifth aspect of the present invention, in the communication system according to the first or the second aspect of the present invention, the receiving device further includes a display and an operating unit, and when the extractor extracts the two or more biological information measuring devices as the communication candidates, the selector is configured to: (a) compare a first radio field intensity with a second radio field intensity, regarding a first biological information measuring device that transmits the pairing signal at the first radio field intensity largest among the two or more biological information measuring devices and a second biological information measuring device that transmits the pairing signal at the second radio field intensity, the second radio field intensity being a second largest radio field intensity; (b-1) select the first biological information measuring device when a difference between the first and the second radio field intensities is larger than a specific level of match; and (b-2) cause the display to display two or more identification indices corresponding to the respective two or more biological information measuring devices to select the biological information measuring device based on an input operation from the operating unit by an operator when the difference between the first and the second radio field intensities is smaller than the specific level of match.

According to a sixth aspect of the present invention, in the communication system according to the fourth or the fifth aspect of the present invention, the display is configured to arrange and display the two or more identification indices of the two or more biological information measuring devices in an order of larger radio field intensity.

According to a seventh aspect of the present invention, in the communication system according to any one of the fourth to the sixth aspect of the present invention, the display is configured to also display information that quantitatively expresses the respective radio field intensities of the corresponding two or more biological information measuring devices together with the two or more identification indices.

According to an eighth aspect of the present invention, in the communication system according to any one of the first to the seventh aspect of the present invention, the receiving device preliminary registers an ID of the at least one biological information measuring device, and the extractor is configured to compare the second threshold value with the radio field intensities of the respective pairing signals transmitted by the respective biological information measuring devices, the extractor being configured to extract the at least one biological information measuring device transmitting the pairing signal at the radio field intensity exceeding the second threshold value, the ID being registered with the at least one biological information measuring device as the communication candidate.

According to a ninth aspect of the present invention, in the communication system according to any one of the first to the eighth aspect of the present invention, the plurality of biological information measuring devices configured to transmit the plurality of pairing signals and the receiving device are disposed in one facility.

According to a tenth aspect of the present invention, there is provided a receiving device that receives a plurality of pairing signals transmitted from a plurality of biological information measuring devices, the receiving device selecting the one biological information measuring device as a communication target among the plurality of biological information measuring devices to establish wireless communications, the receiving device receiving a biological information signal transmitted from the one biological information measuring device, the receiving device including: a detector configured to detect radio field intensities of the plurality of received pairing signals; an extractor configured to compare a second threshold value with the radio field intensities of the plurality of pairing signals, the second threshold value being larger than a first threshold value, the first threshold value specifying a lower limit of the radio field intensity at which transmission of biological information is effectively achieved, the extractor being configured to extract at least the one biological information measuring device transmitting the pairing signal at the radio field intensity exceeding the second threshold value as a communication candidate for the receiving device; a selector configured to select the one biological information measuring device as a communication target among the at least one extracted biological information measuring device; and a communication unit configured to receive the biological information signal transmitted from the one biological information measuring device by the wireless communications.

Advantageous Effects of Invention

A communication system according to the first aspect to the ninth aspect of the present invention includes an extractor to extract communication candidates among a plurality of biological information measuring devices by a receiving device. The extractor compares radio field intensities of a plurality of pairing signals with a second threshold value larger than a first threshold value. The first threshold value specifies a lower limit of the radio field intensity at which a transmission of biological information is effectively achieved. The extractor extracts at least the one biological information measuring device transmitting the pairing signal at the radio field intensity exceeding the second threshold value as the communication candidate for this receiving device. A selector selects the one biological information measuring device as a communication target among the communication candidates extracted by the extractor.

In view of this, the aspect of the present invention restrains the number of the biological information measuring devices becoming the communication candidates compared with another aspect where the extractor extracts the at least one biological information measuring device transmitting the pairing signal at the radio field intensity exceeding the first threshold value as the communication candidate for this receiving device. Consequently, the aspect of the present invention ensures reducing a risk of performing the pairing processing on an incorrect pair.

The receiving device according to the tenth aspect of the present invention is a receiving device applicable to the communication system according to the first aspect to the ninth aspect.

DESCRIPTION OF EMBODIMENTS

Figure 1:
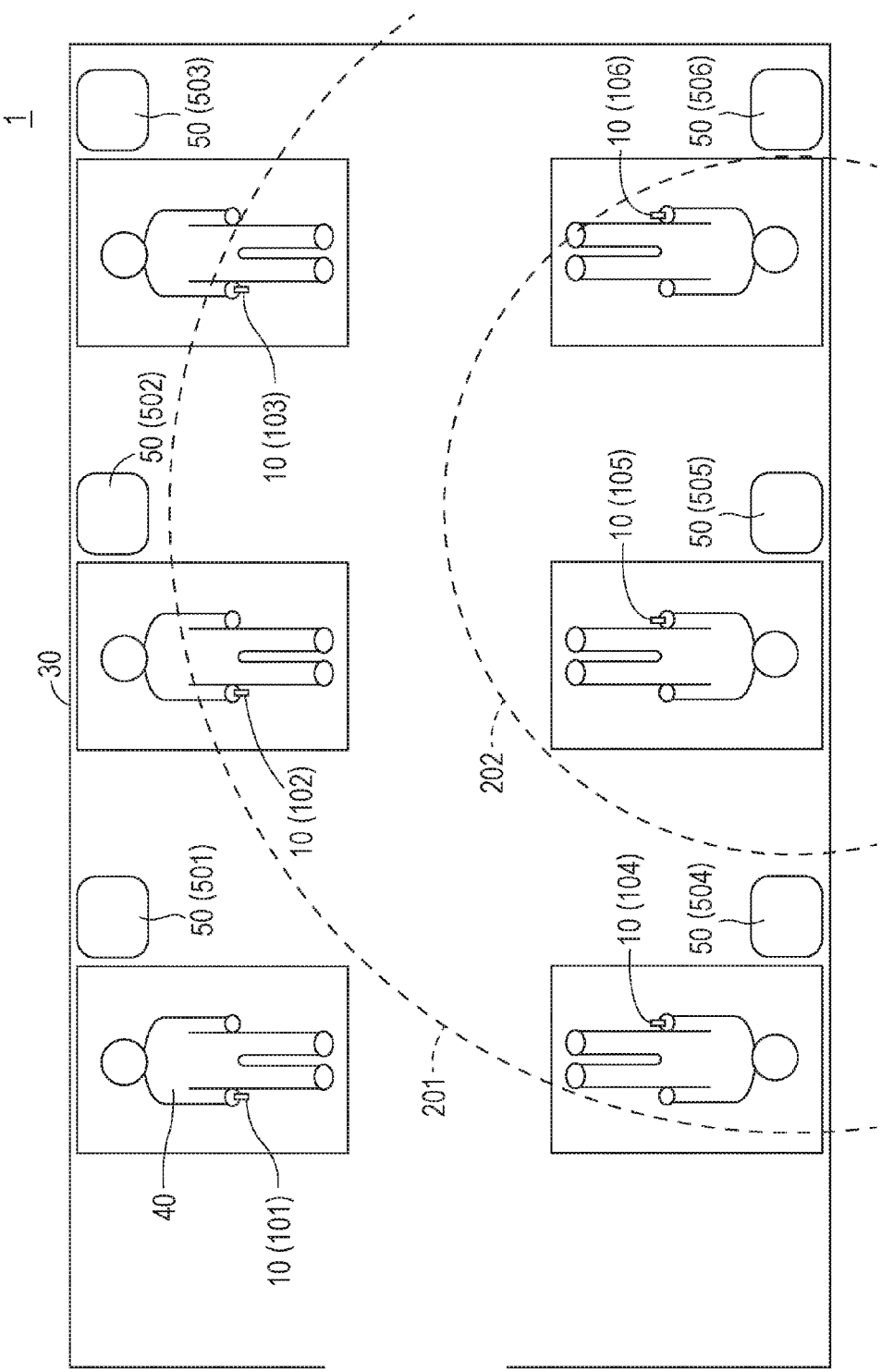
FIG. 1 is a drawing illustrating an example of a communication system 1 in a hospital room 30.

The following describes an embodiment of the present invention based on the drawings. It should be noted that components having a similar structure and function bear the identical reference sign in the drawings, and repetition of description thereof is avoided below. The drawings are schematic, and the sizes, positional relations, and other factors of various structures in each drawing are not accurately drawn.

1 One Embodiment

FIG. 1 is a drawing illustrating an example of a communication system 1 in a hospital room 30.

This embodiment describes the case where the communication system 1 includes a plurality of biological information measuring devices 10 (six pulse oximeters) mounted to a plurality of respective living bodies 40 (six subjects in this embodiment) present in the hospital room 30 and at least one receiving device 50 (six monitors in this embodiment).

The following describes the six biological information measuring devices as the biological information measuring devices 10 when expressed without distinction and as biological information measuring devices 101 to 106 when distinguishably expressed. Similarly, the following describes the six receiving devices as the receiving devices 50 when expressed without distinction and as receiving devices 501 to 506 (FIG. 1) when distinguishably expressed.

<1.1 Configuration of Biological Information Measuring Device 10>

Figure 2:
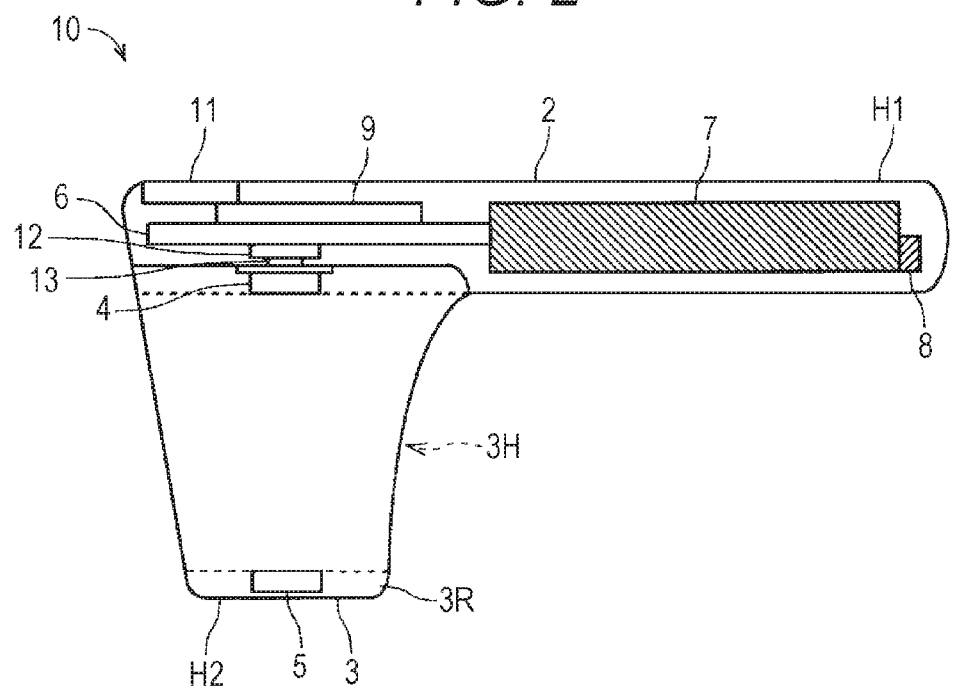
FIG. 2 is a vertical cross-sectional view of a biological information measuring device 10.
Figure 3:
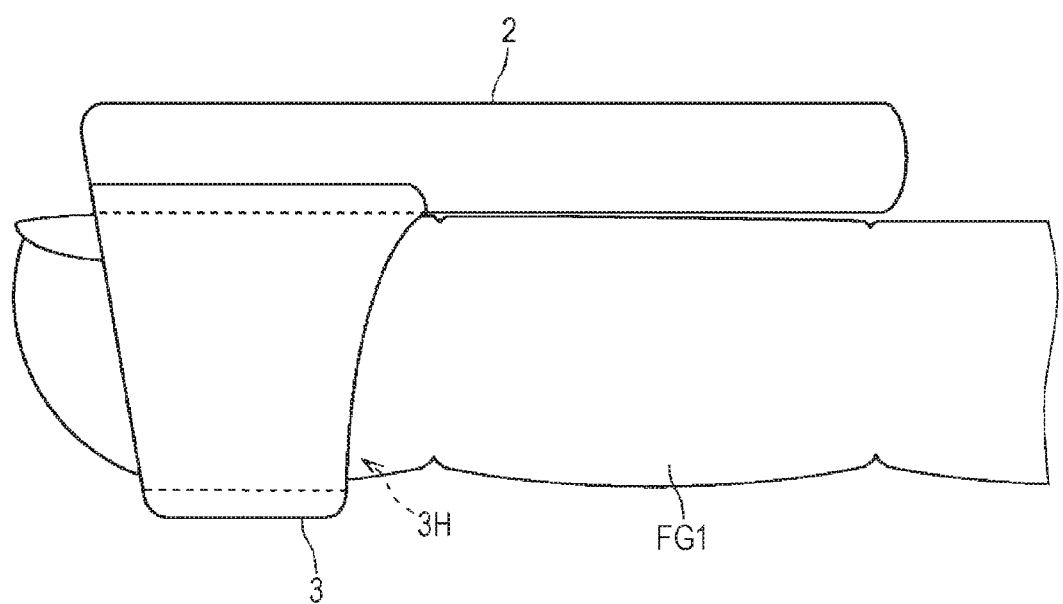
FIG. 3 is a side view illustrating the biological information measuring device 10 mounted to a living body 40.

FIG. 2 is a vertical cross-sectional view schematically illustrating an internal constitution of the biological information measuring device 10. FIG. 3 is a side view schematically illustrating a state where the biological information measuring device 10 is mounted to a finger FG1 of the living body 40 (a human in this embodiment).

The biological information measuring device 10 is a pulse oximeter that acquires a digital value (an SpO2 value) regarding oxygen saturation in blood based on a signal output from a light receiver 5 when this light receiver 5 receives light emitted from a light emitter 4 and transmitting the finger FG1.

The biological information measuring device 10 includes a main body 2 and a mounter 3. As described above, the biological information measuring device 10 includes the light emitter 4 and the light receiver 5. These light emitter 4 and light receiver 5 are opposed interposing a region where the finger FG1 is disposed when the mounter 3 is mounted to the finger FG1.

The main body 2 includes a housing H1 and various components disposed in this housing H1. The various components disposed inside this housing H1 include a function circuit 6, a power supply 7, a charging circuit 8, a communication unit 9, an operating unit 11, and a terminal 12. The housing H1, for example, has an approximately rectangular parallelepiped shape. The terminal 12 is electrically connected to the function circuit 6.

The mounter 3 is mounted integrally with the main body 2. The mounter 3 is a part to be mounted to the finger FG1 of the living body for measurement of various pieces of information on the living body. This mounter 3 includes the light emitter 4, the light receiver 5, and a terminal 13 electrically connected to the light emitter 4 and the light receiver 5. The terminal 13 and the terminal 12 are electrically connected.

In the case where the mounter 3, for example, includes an elastic body that generates an elastic force to hold the finger FG1, the biological information measuring device 10 is easily mounted to the finger FG1. As this elastic body, for example, a high-polymer material such as rubber and a spring and the like can be employed. Specifically, for example, an aspect where the almost entire mounter 3 is made of elastic resin such as rubber, an aspect where an approximately U-shaped leaf spring is embedded into resin, and the like can be employed.

The mounter 3, for example, includes an annular portion 3R with an insertion hole 3H into which the finger FG1 of the living body is inserted into an −X-direction. The insertion hole 3H is a region where the finger FG1 is disposed when the mounter 3 is mounted to the finger FG1. In this case, the insertion of the finger FG1 into the insertion hole 3H ensures considerably easy mounting of the biological information measuring device 10 to the finger FG1 (FIG. 3). An application of a configuration that deforms the annular portion 3R in the insertion hole 3H closing direction by the elastic force generated by the elastic body of the mounter 3 can stably mount the biological information measuring device 10 to the finger FG1.

Figure 4:
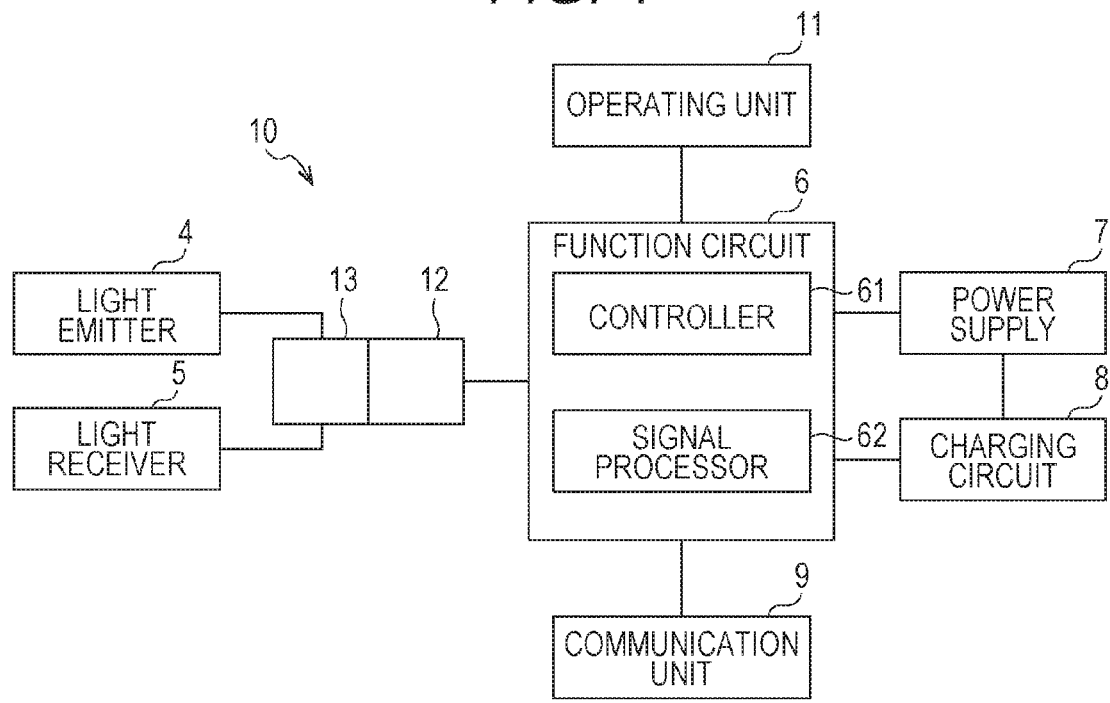
FIG. 4 is a drawing schematically illustrating an electrical configuration of the biological information measuring device 10.
Figure 5:
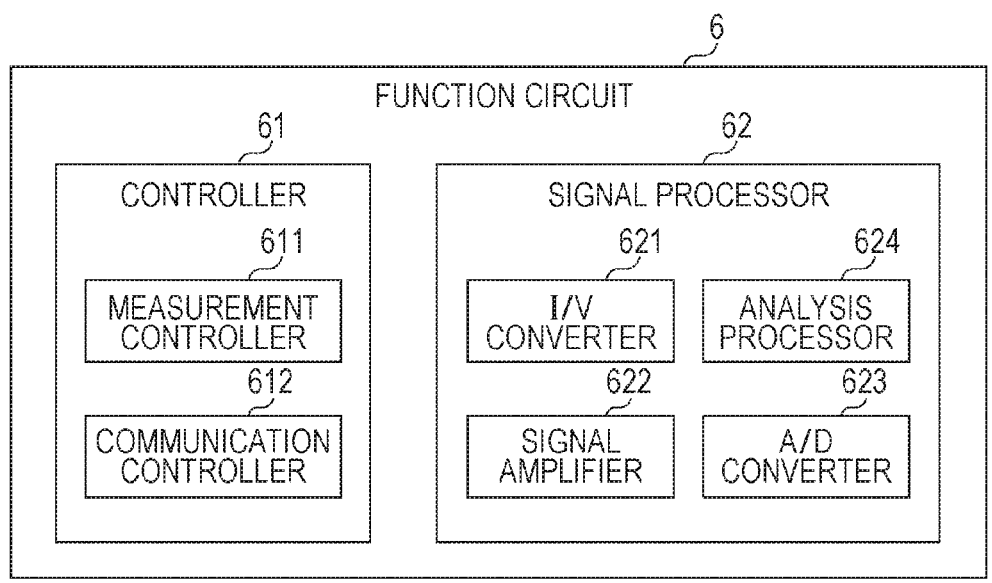
FIG. 5 is a drawing schematically illustrating an electrical configuration of a function circuit 6.

FIGS. 4 and 5 are block diagrams illustrating a functional configuration of the biological information measuring device 10.

As illustrated in FIG. 4, the biological information measuring device 10 includes the light emitter 4, the light receiver 5, the function circuit 6, the power supply 7, the charging circuit 8, the communication unit 9, and the operating unit 11.

The light emitter 4 is electrically connected to the terminal 13. The terminal 13 is electrically connected to the terminal 12, and this terminal 12 is electrically connected to the function circuit 6. This electrically connects the light emitter 4 to the function circuit 6. The power supply 7 supplies electric power to this light emitter 4 according to a control by the function circuit 6 and then the light emitter 4 emits light to the light receiver 5. The light emitter 4 includes a part emitting the light with a wavelength in red region and a part emitting the light with a wavelength of infrared. As such light emitter 4, for example, a Light Emitting Diode (an LED) or the like can be employed. During the measurement, the light emitter 4 emits the red light and the infrared light in alternation.

The light receiver 5 is electrically connected to the terminal 13. This electrically connects the light receiver 5 to the function circuit 6. This light receiver 5 outputs a current signal with magnitude corresponding to an intensity of the received light to a signal processor 62, which will be described later. The light receiver 5, for example, at least includes a photoelectric conversion element such as a silicon photodiode that has sensitivity with respect to the red light and the infrared light. With the finger FG1 inserted into the insertion hole 3H, the light receiver 5 receives the light that has transmitted a biological tissue of the finger FG1 among the red light and the infrared light emitted from the light emitter 4.

During the measurement of the biological information, the light emitter 4 emits the red light and the infrared light in alternation, and the light receiver 5 performs a light-receiving operation synchronized with the light-emitting operation by the light emitter 4. A controller 61, which will be described later, can control the light-emitting operation by the light emitter 4 and the light-receiving operation by the light receiver 5. The light-projecting/receiving operations of the red light and the infrared light are repeated in cycles, for example, around 1/100 (second) or more to 1/30 (second) or less.

The function circuit 6 includes the controller 61 and the signal processor 62. It is only necessary that this function circuit 6 be constituted of various electronic components, integrated-circuit components, a CPU, and the like. As illustrated in FIG. 5, the controller 61 includes a measurement controller 611, a communication controller 612, and a charging circuit controller (not illustrated). The signal processor 62 includes a current-voltage converter (hereinafter referred to as an I/V converter) 621, a signal amplifier 622, an analog-digital converter (hereinafter referred to as an A/D converter) 623, and an analysis processor 624.

The measurement controller 611 controls the operations of the light emitter 4 and the light receiver 5. Here, the measurement controller 611 causes the light emitter 4 to emit the respective red light and infrared light in alternation at the cycle of, for example, 1/100 (second). The communication controller 612 controls data communications between the communication unit 9 in the biological information measuring device 10 and a communication unit 60 in the receiving device 50.

The I/V converter 621 converts the current signals periodically output from the light receiver 5 into voltage signals. This voltage signal is a signal regarding an analog pulse wave (also referred to as a pulse wave signal).

The signal amplifier 622 is, for example, an amplifier that amplifies the voltage signals output from the I/V converter 621.

The A/D converter 623 converts the analog pulse wave signals output from the signal amplifier 622 into digital pulse wave signals. This obtains digital values regarding the pulse wave. That is, when the light receiver 5 receives the light that has emitted from the light emitter 4 and transmitted the finger FG1, the digital value regarding the pulse wave can be acquired based on the current signal output from the light receiver 5.

The analysis processor 624 analyzes predetermined data based on the digital pulse wave signals output from the A/D converter 623. This calculates various values: amounts of light of the red light and the infrared light received by the light receiver 5, the amplitude of the pulse wave, a ratio of the amplitude of the red light to the amplitude of the infrared light, a value of the oxygen saturation in blood (the SpO2 value), a pulse rate, an interval of the pulse wave (a cycle), and the like.

The measurement controller 611, the communication controller 612, and the analysis processor 624 may be constituted of a dedicated electronic circuit or may be achieved by execution of programs in a microprocessor, a Digital Signal Processor (DSP), and the like. The I/V converter 621, the signal amplifier 622, and A/D converter 623 can be, for example, constituted of a dedicated electronic circuit.

The power supply 7 includes, for example, a secondary battery such as a nickel hydrogen storage battery and a lithium-ion battery. The power supply 7 supplies the electric power to the various components in the biological information measuring device 10 such as the light emitter 4 and the function circuit 6. This ensures eliminating a need for a mechanism to exchange a primary battery such as a dry battery for the main body 2. This ensures achieving a simple configuration of the main body 2 that is less likely to be broken.

The charging circuit 8 is a circuit that charges the secondary battery of the power supply 7. For example, a configuration that couples a charger to a terminal electrically connected to the secondary battery to charge the secondary battery is considered. This allows charging the secondary battery with the simple configuration. For example, in the case where the charging circuit 8 contactlessly charges the secondary battery, that is, in the case where the charging circuit 8 includes a circuit for contactless charging to the secondary battery, a terminal or the like to couple the charger or the like is unnecessary. This allows charging to the secondary battery with a simpler configuration. As the contactless charging method, for example, a method using electromagnetic induction by a coil and the like and other methods can be employed.

The communication unit 9 transmits a pairing signal including pairing information to establish wireless communications and the biological information signal including the data acquired by the signal processor 62 by wireless communications. When the pairing processing, which will be described later, establishes the wireless communications between the biological information measuring device 10 and the receiving device 50, the communication unit 60 (FIG. 7) in the receiving device 50 receives the biological information signal transmitted from the communication unit 9 in the biological information measuring device 10. The receiving device 50 stores the data and displays the measurement results. Thus, performing at least some data processes by the receiving device 50 ensures downsizing, power-saving, and reduction in production cost of the biological information measuring device 10.

The following assumes the case where the signal processor 62 acquires the digital values regarding at least one kind or more of the value of the oxygen saturation in blood (the SpO2 value), the pulse rate, and the interval of the pulse wave (the cycle) based on the digital pulse wave signals. In this case, the communication unit 9 transmits the digital value data regarding at least one kind or more of the value of the oxygen saturation in blood (the SpO2 value), the pulse rate, and the interval of the pulse wave (the cycle) acquired by the signal processor 62 as the biological information signal. This allows this receiving device 50 to easily acquire beneficial information without performing a special operation and the like by the receiving device 50, which receives the biological information signal transmitted from the communication unit 9.

The function circuit 6 may include various memories storing the data acquired by the signal processor 62.

The operating unit 11 includes, for example, a power supply button, a measurement start button, a measurement end button, and a pairing start button. The power supply button is a button to switch presence/absence of the supply of electric power from the power supply 7 to the respective units in the biological information measuring device 10. The measurement start button is a button to start the measurement of the value of the oxygen saturation in blood (the SpO2 value) or the like. The measurement end button is a button to end the measurement of the value of the oxygen saturation in blood (the SpO2 value) or the like. The pairing start button is a button to start the pairing processing, which will be described later. Pressing the pairing start button wirelessly transmits the pairing signal from the communication unit 9.

<1.2 Receiving Device 50>

Figure 6:
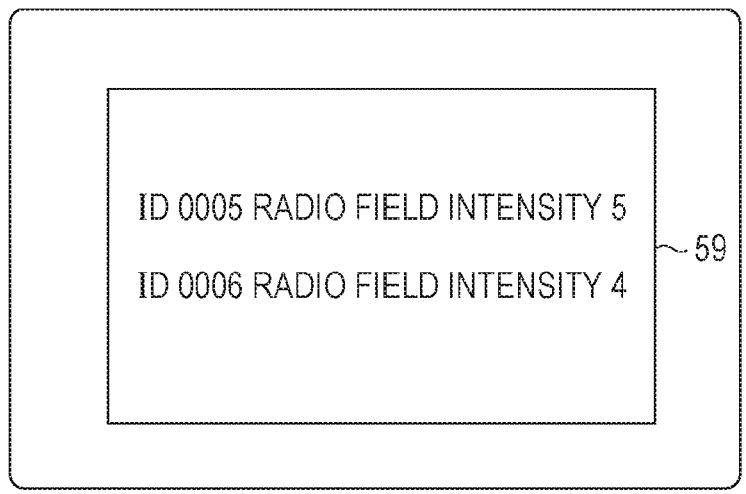
FIG. 6 is a drawing illustrating an appearance of a receiving device 50.
Figure 7:
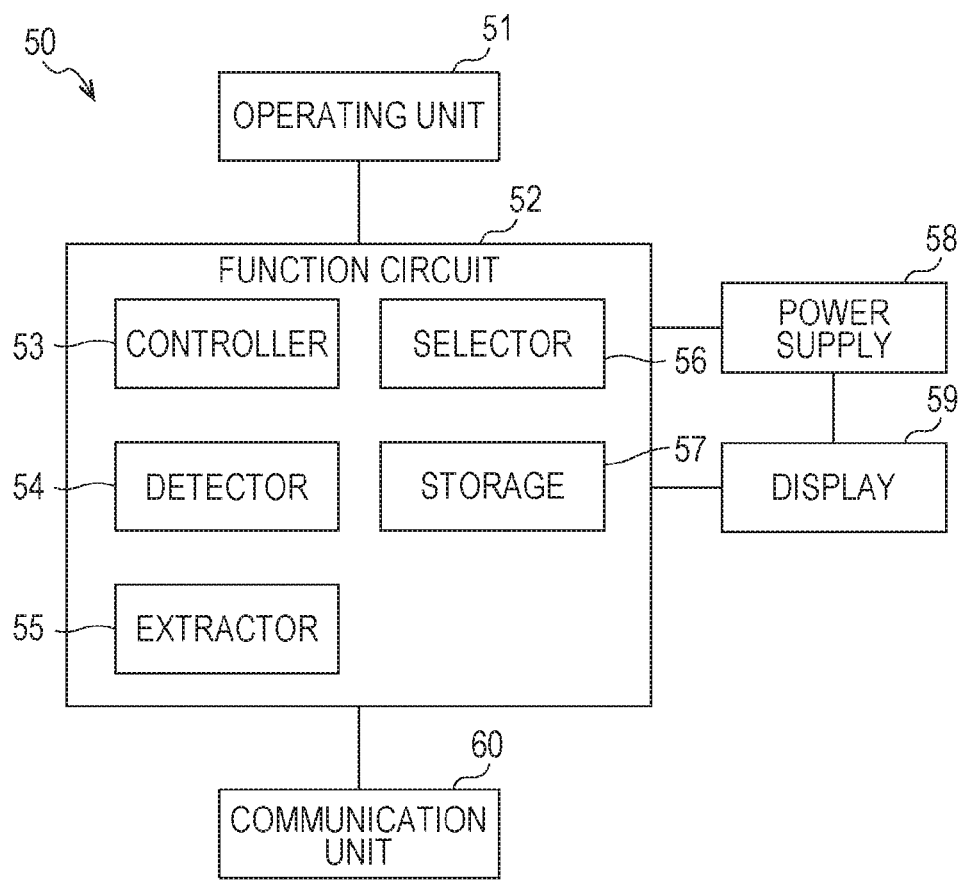
FIG. 7 is a drawing schematically illustrating an electrical configuration of the receiving device 50.

FIG. 6 is a front view illustrating a display 59 of the receiving device 50. FIG. 7 is a block diagram illustrating a functional configuration of the receiving device 50.

The receiving device 50 is a device that receives the plurality of pairing signals transmitted from the plurality of biological information measuring devices 10 and establishes the wireless communications with the one biological information measuring device 10 as a communication target. After that, the receiving device 50 receives the biological information signal transmitted from this one biological information measuring device 10 by the wireless communications. In this embodiment, the receiving device 50 is a monitor that displays the biological information corresponding to the received biological information signal on the display 59.

The receiving device 50 includes an operating unit 51, a function circuit 52, a power supply 58, the display 59, and the communication unit 60.

The operating unit 51 is constituted of a keyboard, a computer mouse, a touchscreen, and the like. The operating unit 51 is used for input processing to the receiving device 50 by the operator of the receiving device 50.

The function circuit 52 includes a controller 53, a detector 54, an extractor 55, a selector 56, and a storage 57. It is only necessary that this function circuit 52 be constituted of various electronic components, integrated-circuit components, a CPU, and the like.

The controller 53 includes a communication controller and a display controller. The communication controller controls data communications between the communication unit 9 in the biological information measuring device 10 and the communication unit 60 in the receiving device 50. The display controller controls display contents on the display 59.

The detector 54, the extractor 55, and the selector 56 are functional units mainly related to the pairing processing; therefore, the details are described in <1.3 Pairing Processing>, which will be described later.

The communication unit 60 receives the plurality of pairing signals transmitted from the plurality of biological information measuring devices 10. The plurality of pairing signals received by the communication unit 60 are provided to the detector 54 and the pairing processing, which will be described later, is performed. When the wireless communications are thus established, the communication unit 60 receives the biological information signal transmitted from the communication unit 9 in the one biological information measuring device 10 as the communication target. The communication unit 60 provides this biological information signal (the digital value of the biological information acquired by the signal processor 62) to the controller 53 and the storage 57.

The controller 53 performs the display control to the display 59 based on this digital value. Consequently, the display 59 displays at least one kind or more pieces of biological information among the value of the oxygen saturation in blood (the SpO2 value), the pulse rate, and the interval of the pulse wave (the cycle) as visual information.

The storage 57 includes the various memories and stores the data regarding the biological information signal received by the communication unit 60. The data stored by the storage 57 may be used by an external device of the receiving device 50.

The power supply 58 includes an outlet to receive electric power from outside the receiving device 50. The power supply 58, for example, receives the electric power from a commercial power supply via a power supply cord. The power supply 58 supplies the electric power to the respective units constituting the receiving device 50.

<1.3 Pairing Processing>

Figure 8:
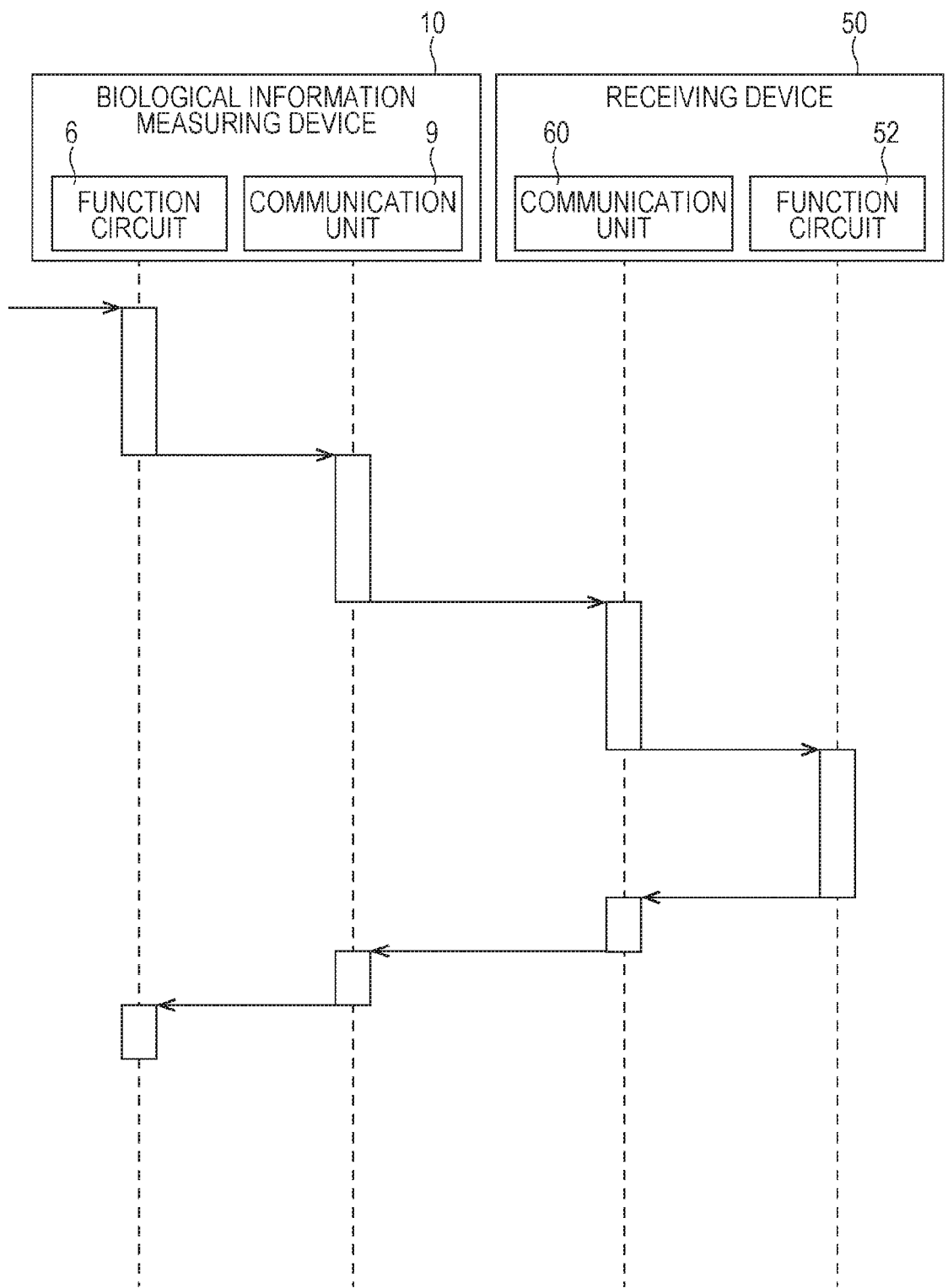
FIG. 8 is a drawing illustrating a timing chart of pairing processing.

FIG. 8 is a timing chart of the pairing processing performed between the biological information measuring device 10 and the receiving device 50. The pairing processing means a sequence of processes to store the pairing information (such as ID information and channel information) of the one biological information measuring device 10 as the communication target by the one receiving device 50.

A trigger to start the pairing processing is to press the pairing start button of the biological information measuring device 10 by the operator. Accordingly, the controller 61 in the function circuit 6 controls the communication unit 9, and the communication unit 9 wirelessly transmits the pairing signal including the pairing information.

The following assumes the case where the pairing start buttons are pressed in the respective six biological information measuring devices 10 in the hospital room 30 illustrated in FIG. 1 and the six pairing signals are wirelessly transmitted. In this situation, the following describes the case where the pairing processing is performed between the biological information measuring device 105 and the receiving device 505.

The communication unit 60 in the receiving device 505 receives the six pairing signals wirelessly transmitted from the respective communication units 9. Triggered by the reception of the pairing signals by the receiving device 50, the receiving device 50 enters a routine to establish the wireless communications. The communication unit 60 provides the six pairing signals to the function circuit 52 (FIGS. 7 and 8).

The detector 54 measures amplitude values of the six pairing signals received by the communication unit 60. Based on the measurement results, the detector 54 detects radio field intensities of the respective six pairing signals. The detector 54 provides information on the detected radio field intensities to the extractor 55.

The extractor 55 compares the radio field intensities of the six pairing signals with a second threshold value. The extractor 55 extracts the at least one biological information measuring device 10 transmitting the pairing signal at the radio field intensity exceeding the second threshold value as a communication candidate for the receiving device 505. The second threshold value is a threshold value larger than a first threshold value that specifies a lower limit of the radio field intensity at which the transmission of the biological information is effectively achieved and is a threshold value preset in the storage 57.

FIG. 1 illustrates a first range 201 and a second range 202 viewed from the receiving device 505. The first range 201 means a space range in which the biological information measuring devices 10 that transmit the pairing signals at the radio field intensity exceeding the first threshold value to the receiving device 505 are present. The second range 202 means a space range in which the biological information measuring devices 10 that transmit the pairing signals at the radio field intensity exceeding the second threshold value to the receiving device 505 are present. Since the second threshold value is set to be a value larger than the first threshold value, the second range 202 is a range narrower than the first range 201 (more specifically, a range close to the receiving device 505).

The second range 202 for the receiving device 505 includes the biological information measuring devices 105 and 106 as the biological information measuring devices 10 that transmit the pairing signals at the radio field intensity larger than the second threshold value (FIG. 1).

In view of this, the extractor 55 in the receiving device 505 extracts the two biological information measuring devices 105 and 106 as the communication candidates for this receiving device 505.

With case where the extractor 55 extracting the two or more biological information measuring devices 10 as the communication candidates, the selector 56 is a part that causes the display 59 to display two or more identification indices corresponding to the respective two or more biological information measuring devices extracted as the communication candidates. Accordingly, in this embodiment, the selector 56 causes the display 59 to display the two identification indices (ID0005 and ID0006) corresponding to the respective two biological information measuring devices 105 and 106 (FIG. 6).

The display 59 arranges and displays the two or more identification indices of the two or more biological information measuring devices 10 as the communication candidates in the order of the larger radio field intensity. Accordingly, in this embodiment, the display 59 arranges and displays the two identification indices (ID0005 and ID0006) of the two biological information measuring devices 105 and 106 as the communication candidates in the order of larger radio field intensity (FIG. 6). This allows the operator to easily recognize the mutual relationship between the radio field intensities and the two or more biological information measuring devices 10 as the communication candidates.

The display 59 also displays information that quantitatively expresses the respective radio field intensities of the corresponding two or more biological information measuring devices (radio field intensity information) together with the two or more identification indices. Accordingly, in this embodiment, the display 59 displays the radio field intensity information (the radio field intensity 5 and the radio field intensity 4) of the two biological information measuring devices 105 and 106 as the communication candidates (FIG. 6). This allows the operator to further specifically recognize the relationship between the biological information measuring devices 10 as the communication candidates and the radio field intensities generated at these biological information measuring devices 10.

The selector 56 selects the one biological information measuring device 10 as the communication target for the receiving device 50 based on an input operation from the operating unit 51 by the operator. Accordingly, for example, selecting any one of the two identification indices (ID0005 and ID0006), which are displayed on the display 59, by the operator of the receiving device 505 using the operating unit 51 such as the computer mouse (for example, ID0005) determines the biological information measuring device 105 corresponding to the selected identification index as the communication target for this receiving device 505.

Consequently, the storage 57 in the receiving device 505 stores the pairing information on the biological information measuring device 105 as the communication target. Afterwards, the communication unit 60 in the receiving device 505 transmits a positive response (ACK) signal to the communication unit 9 in the biological information measuring device 105. The transmission of the positive response (ACK) signal to the function circuit 6 via the communication unit 9 ends the pairing processing and the wireless communications are established between the biological information measuring device 105 and the receiving device 505.

<1.4 Summary of One Embodiment>

As described above, the communication system 1 includes the extractor 55, which is to extract the communication candidates among the plurality of biological information measuring devices 10 by the receiving device 50. The extractor 55 compares the radio field intensities of the plurality of pairing signals with the second threshold value, which is larger than the first threshold value. The extractor 55 extracts the at least one biological information measuring device 10 transmitting the pairing signal at the radio field intensity exceeding the second threshold value as the communication candidate for this receiving device 50. According to the input operation by the operator, the selector 56 selects the one biological information measuring device 10 as the communication target among the communication candidates extracted by the extractor 55.

In view of this, the aspect of this embodiment restrains the number of the biological information measuring devices 10 selected as the communication candidates compared with another aspect where the extractor extracts the at least one biological information measuring device transmitting the pairing signal at the radio field intensity exceeding the first threshold value as the communication candidate for this receiving device. More specifically, in the state of FIG. 1, while the aspect of this embodiment extracts only the two biological information measuring devices 105 and 106 as the communication candidates for the receiving device 505, the above-described other aspect extracts the five biological information measuring devices 102 to 106 as the communication candidates for the receiving device 505. Consequently, the aspect of this embodiment ensures reducing a risk of performing the pairing processing on an incorrect pair caused by the presence of a large number of communication candidates.

The effect that reduces the risk of performing the pairing processing on the incorrect pair is especially effective in the case where the respective biological information measuring devices 10 and receiving devices 50, which constitute the communication system 1, are disposed in one facility (for example, a medical facility and a nursing home). This is because, in the case where the communication system 1 is thus used in one facility, probably a large number of the biological information measuring devices 10 that transmit the pairing signals at the radio field intensity exceeding the first threshold value are present viewed from the receiving device 50.

To establish the communications between the receiving device 50 and the one biological information measuring device 10 as the communication target for this receiving device 50 in the field where the communication system 1 is used (for example, the hospital room 30), generally, this receiving device 50 is disposed close to this one biological information measuring device 10 and the pairing processing is performed. Therefore, a situation that the radio field intensity of the pairing signal transmitted by this one biological information measuring device 10 is smaller than the second threshold value (in other words, this one biological information measuring device 10 is not extracted as the communication candidate) is less likely to occur.

As illustrating in FIG. 1, the first range 201 is wider than the second range 202. In view of this, after the communications between the biological information measuring device 105 and the receiving device 505 are established with the biological information measuring device 105 positioned in the second range 202 for the receiving device 505, as long as the biological information measuring device 105 is positioned in the first range 201 for the receiving device 505, a distance between both may be increased. This is because, as long as the biological information measuring device 105 is positioned in the first range 201 for the receiving device 505, the biological information measuring device 105 effectively achieves the transmission of the biological information signal to the receiving device 505. Accordingly, this embodiment reduces the restriction on a movement range of the living body 40 to which the biological information measuring device 105 is mounted after the communications have been established.

<2 Modification>

It should be noted that the present invention is in no way limited to the above-described embodiment, and can be implemented by making various modifications, improvements, and the like without departing from the scope of the present invention.

The one embodiment describes the aspect that the selector 56 selects the one biological information measuring device 10 as the communication target based on the input operation by the operator (a manual selection aspect); however, this should not be construed in a limiting sense.

An aspect that the selector 56 automatically selects the one biological information measuring device 10 as the communication target (an automatic selection aspect) may also be applicable. As the automatic selection aspect, the following aspect may be applicable. For example, when the extractor 55 extracts the two or more biological information measuring devices 10 as the communication candidates, the selector 56 selects the one biological information measuring device 10 that transmits the pairing signal at the largest radio field intensity as the communication target among the two or more biological information measuring devices 10.

As another example, the following aspect may be applicable. When a specific condition is met, the selector 56 automatically selects the one biological information measuring device 10 as the communication target. When the condition is not met, the selector 56 selects the one biological information measuring device 10 as the communication target based on the input operation by the operator. For example, regarding a first biological information measuring device that transmits the pairing signal at first radio field intensity, largest among the two or more biological information measuring devices 10, and a second biological information measuring device that transmits the pairing signal at second radio field intensity, the second largest radio field intensity, the selector 56 compares the first radio field intensity with the second radio field intensity. When a difference between the first and the second radio field intensities is larger than a specific level of match, the selector 56 automatically selects the first biological information measuring device. When the difference between the first and the second radio field intensities is smaller than the specific level of match, the selector 56 selects the one biological information measuring device based on the input operation by the operator. Various methods can be employed to calculate the level of match such as a difference or a ratio between the first and the second radio field intensities or a combination of the difference and the ratio.

The one embodiment describes the aspect that the extractor 55 extracts all the biological information measuring devices 10 transmitting the pairing signals at the radio field intensity exceeding the second threshold value as the communication candidates; however, this should not be construed in a limiting sense.

The following aspect may be applicable. The extractor 55 further has an extraction condition different from the radio field intensity. The extractor 55 extracts the biological information measuring device 10 that transmits the pairing signal at the radio field intensity exceeding the second threshold value and meets the extraction condition as the communication candidate. For example, the following aspect may be applicable. The storage 57 in the receiving device 50 preliminary registers an ID of the at least one biological information measuring device 10. The extractor 55 extracts the at least one biological information measuring device 10 that transmits the pairing signal at the radio field intensity exceeding the second threshold value and with which the ID is registered as the communication candidate. This aspect can remove the biological information measuring devices 10 with which the ID is not registered from the communication candidate. This ensures further restraining the number of communication candidates. This is especially effective in the case where a large number of the biological information measuring devices 10 are present around the one receiving device 50 (for example, the biological information measuring devices 10 are also present in the adjacent hospital rooms like a hospital).

The one embodiment describes the case of the use of the pulse oximeter as the biological information measuring device 10; however, this should not be construed in a limiting sense. As the biological information measuring device 10, various biological information measuring devices such as an electrocardiographic monitor and a blood pressure monitor are applicable. Similarly, as the receiving device 50 as well, various receiving devices such as a personal computer and a tablet are applicable in addition to the monitor.

The one embodiment describes the aspect that, while the biological information measuring device 10 transmits the pairing signal and the biological information signal to the receiving device 50, the receiving device 50 transmits only the positive response (ACK) signal to the biological information measuring device 10. However, this should not be construed in a limiting sense. The receiving device 50 may transmit a control signal to the biological information measuring device 10. For example, the receiving device 50 transmits a signal to control powering-off of the biological information measuring device 10 to the biological information measuring device 10.

The one embodiment describes the aspect that the communication system 1 includes the plurality of biological information measuring devices 10 and receiving devices 50; however, this should not be construed in a limiting sense. For example, an aspect that the communication system 1 includes the one biological information measuring device 10 and the one receiving device 50 may be applicable. In this case, similar to the above-described one embodiment, the extractor 55 may select the communication target, or the communication target may be selected by another method different from the above-described one embodiment. As the other method, for example, a method that automatically selects the one biological information measuring device 10 as the communication target is applicable.

It should be appreciated that all or part of the one embodiment and various modifications set forth above can appropriately be combined with one another within a reasonable scope.

REFERENCE SIGNS LIST

1: Communication system
9: Communication unit 10, 101 to 106: Biological information measuring device
30: Hospital room
40: Living body
50, 501 to 506: Receiving device
53: Controller
54: Detector
55: Extractor
56: Selector
57: Storage
60: Communication unit
201: First range
202: Second range

The invention claimed is:

1. A communication system comprising:
a biological information measuring device configured to transmit a pairing signal and a biological information signal by wireless communications, the pairing signal including pairing information to establish the wireless communications, the biological information signal including biological information acquired through measurement; and
a receiving device configured to receive the pairing signal transmitted from the biological information measuring device, the receiving device being configured to establish the wireless communications with the biological information measuring device to receive the biological information signal transmitted from the biological information measuring device, wherein the receiving device includes:
a detector configured to detect a radio field intensity of the received pairing signal;
an extractor configured to compare a second threshold value with the radio field intensities of the plurality of pairing signals when the plurality of pairing signals are detected by the detector, the second threshold value being larger than a first threshold value, the first threshold value specifying a lower limit of the radio field intensity at which the transmission of the biological information is effectively achieved, the extractor being configured to extract the at least one biological information measuring device transmitting the pairing signal at the radio field intensity exceeding the second threshold value as a communication candidate for the receiving device;
a selector configured to select the biological information measuring device as a communication target among the at least one extracted biological information measuring device; and
a communication unit configured to receive the biological information signal transmitted from the biological information measuring device by the wireless communications.

2. The communication system according to claim 1, wherein the receiving device is configured to enter a routine to establish the wireless communications triggered by the reception of the pairing signal transmitted from the biological information measuring device by the receiving device.

3. The communication system according to claim 2, wherein the selector is configured to select the biological information measuring device that transmits the pairing signal at a largest radio field intensity among the two or more biological information measuring devices when the extractor extracts the two or more biological information measuring devices as the communication candidates.

4. The communication system according to claim 2, wherein:
the receiving device further includes a display and an operating unit, and
when the extractor extracts the two or more biological information measuring devices as the communication candidates, the selector is configured to cause the display to display two or more identification indices corresponding to the respective two or more biological information measuring devices extracted as the communication candidates, the selector being configured to select the biological information measuring device based on an input operation from the operating unit by an operator.

5. The communication system according to claim 2, wherein:
the receiving device further includes a display and an operating unit, and
when the extractor extracts the two or more biological information measuring devices as the communication candidates, the selector is configured to:
(a) compare a first radio field intensity with a second radio field intensity, regarding a first biological information measuring device that transmits the pairing signal at the first radio field intensity largest among the two or more biological information measuring devices and a second biological information measuring device that transmits the pairing signal at the second radio field intensity, the second radio field intensity being a second largest radio field intensity;
(b-1) select the first biological information measuring device when a difference between the first and the second radio field intensities is larger than a specific level of match; and
(b-2) cause the display to display two or more identification indices corresponding to the respective two or more biological information measuring devices to select the biological information measuring device based on an input operation from the operating unit by an operator when the difference between the first and the second radio field intensities is smaller than the specific level of match.

6. The communication system according to claim 2, wherein:
the receiving device preliminary registers an ID of the at least one biological information measuring device, and
the extractor is configured to compare the second threshold value with the radio field intensities of the respective pairing signals transmitted by the respective biological information measuring devices, the extractor being configured to extract the at least one biological information measuring device transmitting the pairing signal at the radio field intensity exceeding the second threshold value, the ID being registered with the at least one biological information measuring device as the communication candidate.

7. The communication system according to claim 2, wherein the plurality of biological information measuring devices configured to transmit the plurality of pairing signals and the receiving device are disposed in one facility.

8. The communication system according to claim 1, wherein the selector is configured to select the biological information measuring device that transmits the pairing signal at a largest radio field intensity among the two or more biological information measuring devices when the extractor extracts the two or more biological information measuring devices as the communication candidates.

9. The communication system according to claim 8, wherein:

the receiving device preliminary registers an ID of the at least one biological information measuring device, and the extractor is configured to compare the second threshold value with the radio field intensities of the respective pairing signals transmitted by the respective biological information measuring devices, the extractor being configured to extract the at least one biological information measuring device transmitting the pairing signal at the radio field intensity exceeding the second threshold value, the ID being registered with the at least one biological information measuring device as the communication candidate.

10. The communication system according to claim 8, wherein the plurality of biological information measuring devices configured to transmit the plurality of pairing signals and the receiving device are disposed in one facility.

11. The communication system according to claim 1, wherein:

the receiving device further includes a display and an operating unit, and when the extractor extracts the two or more biological information measuring devices as the communication candidates, the selector is configured to cause the display to display two or more identification indices corresponding to the respective two or more biological information measuring devices extracted as the communication candidates, the selector being configured to select the biological information measuring device based on an input operation from the operating unit by an operator.

12. The communication system according to claim 11, wherein the display is configured to arrange and display the two or more identification indices of the two or more biological information measuring devices in an order of larger radio field intensity.

13. The communication system according to claim 11, wherein the display is configured to also display information that quantitatively expresses the respective radio field intensities of the corresponding two or more biological information measuring devices together with the two or more identification indices.

14. The communication system according to claim 11, wherein:

the receiving device preliminary registers an ID of the at least one biological information measuring device, and the extractor is configured to compare the second threshold value with the radio field intensities of the respective pairing signals transmitted by the respective biological information measuring devices, the extractor being configured to extract the at least one biological information measuring device transmitting the pairing signal at the radio field intensity exceeding the second threshold value, the ID being registered with the at least one biological information measuring device as the communication candidate.

15. The communication system according to claim 11, wherein the plurality of biological information measuring devices configured to transmit the plurality of pairing signals and the receiving device are disposed in one facility.

16. The communication system according to claim 1, wherein:

the receiving device further includes a display and an operating unit, and when the extractor extracts the two or more biological information measuring devices as the communication candidates, the selector is configured to:

(a) compare a first radio field intensity with a second radio field intensity, regarding a first biological information measuring device that transmits the pairing signal at the first radio field intensity largest among the two or more biological information measuring devices and a second biological information measuring device that transmits the pairing signal at the second radio field intensity, the second radio field intensity being a second largest radio field intensity;

(b-1) select the first biological information measuring device when a difference between the first and the second radio field intensities is larger than a specific level of match; and (b-2) cause the display to display two or more identification indices corresponding to the respective two or more biological information measuring devices to select the biological information measuring device based on an input operation from the operating unit by an operator when the difference between the first and the second radio field intensities is smaller than the specific level of match.

17. The communication system according to claim 16, wherein the display is configured to arrange and display the two or more identification indices of the two or more biological information measuring devices in an order of larger radio field intensity.

18. The communication system according to claim 1, wherein:

the receiving device preliminary registers an ID of the at least one biological information measuring device, and the extractor is configured to compare the second threshold value with the radio field intensities of the respective pairing signals transmitted by the respective biological information measuring devices, the extractor being configured to extract the at least one biological information measuring device transmitting the pairing signal at the radio field intensity exceeding the second threshold value, the ID being registered with the at least one biological information measuring device as the communication candidate.

19. The communication system according to claim 1, wherein the plurality of biological information measuring devices configured to transmit the plurality of pairing signals and the receiving device are disposed in one facility.

20. A receiving device that receives a plurality of pairing signals transmitted from a plurality of biological information measuring devices, the receiving device selecting the one biological information measuring device as a communication target among the plurality of biological information measuring devices to establish wireless communications, the receiving device receiving a biological information signal transmitted from the one biological information measuring device, the receiving device comprising:

a detector configured to detect radio field intensities of the plurality of received pairing signals;

an extractor configured to compare a second threshold value with the radio field intensities of the plurality of pairing signals, the second threshold value being larger than a first threshold value, the first threshold value specifying a lower limit of the radio field intensity at which transmission of biological information is effectively achieved, the extractor being configured to extract at least the one biological information measuring device transmitting the pairing signal at the radio field intensity exceeding the second threshold value as a communication candidate for the receiving device;

a selector configured to select the one biological information measuring device as a communication target among the at least one extracted biological information measuring device; and a communication unit configured to receive the biological information signal transmitted from the one biological information measuring device by the wireless communications.

* * * * *